(12) United States Patent
Ray et al.

(10) Patent No.: US 7,834,176 B2
(45) Date of Patent: *Nov. 16, 2010

(54) POLYMORPH E OF OLANZAPINE AND PREPARATION OF ANHYDROUS NON-SOLVATED CRYSTALLINE POLYMORPHIC FORM I OF 2-METHYL-4(4-METHYL-1-PIPERAZINYL)-10H-THIENO[2,3-B][1,5] BENZODIAZEPINE (OLANZAPINE FORM I) FROM THE POLYMORPHIC OLANZAPINE FORM E

(75) Inventors: Anup Kumar Ray, Staten Island, NY (US); Hiren Kumar V. Patel, Fords, NJ (US); Johannes Ludescher, Breitenbach (AT); Mahendra R. Patel, Milltown, NJ (US)

(73) Assignee: Sandoz AG, Basel (CH)

( * ) Notice: Subject to any disclaimer, the term of this patent is extended or adjusted under 35 U.S.C. 154(b) by 1267 days.

This patent is subject to a terminal disclaimer.

(21) Appl. No.: 11/340,284

(22) Filed: Jan. 26, 2006

(65) Prior Publication Data

US 2007/0173496 A1 Jul. 26, 2007

(51) Int. Cl.
  *C07D 495/04* (2006.01)
(52) U.S. Cl. .................................................. 540/557
(58) Field of Classification Search ................ 540/557
  See application file for complete search history.

(56) References Cited

U.S. PATENT DOCUMENTS

| | | | |
|---|---|---|---|
| 3,985,750 A | 10/1976 | Protiva et al. | 260/268 TR |
| 4,115,574 A | 9/1978 | Chakrabarti et al. | 424/250 |
| 5,229,382 A | 7/1993 | Chakrabarti et al. | 514/220 |
| 5,605,897 A | 2/1997 | Beasley, Jr. et al. | 514/220 |
| 5,627,178 A | 5/1997 | Chakrabarti | 514/220 |
| 5,631,250 A | 5/1997 | Bunnell et al. | 514/220 |
| 5,637,584 A | 6/1997 | Larsen | 514/220 |
| 5,703,232 A | 12/1997 | Bunnell | 540/557 |
| 5,736,541 A | 4/1998 | Bunnell et al. | 514/220 |
| 5,817,655 A | 10/1998 | Chakrabarti | 514/220 |
| 5,817,656 A | 10/1998 | Beasley | 514/220 |
| 5,817,657 A | 10/1998 | Beasley, Jr. et al. | 514/220 |
| 6,020,487 A | 2/2000 | Bunnell et al. | 540/557 |
| 6,251,895 B1 | 6/2001 | Larsen et al. | 514/220 |
| 7,297,789 B2 * | 11/2007 | Patel et al. | 540/557 |
| 2004/0048854 A1 * | 3/2004 | Patel et al. | 514/220 |
| 2004/0198721 A1 | 10/2004 | Dolitzky | |

FOREIGN PATENT DOCUMENTS

| | | |
|---|---|---|
| EP | 0454436 B1 | 10/1991 |
| EP | 0733367 B1 | 9/1996 |
| EP | 0733635 A1 | 9/1996 |
| EP | 0831098 B1 | 3/1998 |
| WO | WO0218390 | 3/2002 |
| WO | 03097650 | 11/2003 |
| WO | 2004006933 | 1/2004 |
| WO | 2006006185 | 1/2006 |

OTHER PUBLICATIONS

Chakrabarti et al., "10-Piperazinyl-4H-thieno[3,2-b][1,5]-and-[3,4-b][1,5]benzodiazepines as Potential Neuroleptics", J. Med. Chem. vol. 23, pp. 884-889 (1980).

Chakrabarti et al., "4-Piperazinyl-10H-thieno[2,3-b][1,5]benzodiazepines as Potential Neuroleptics", J. Med. Chem. vol. 23, pp. 878-884 (1980).

Chakrabarti et al., "Heteroarene-fused Benzodiazepines. Part 1 Synthesis of Thieno-[2,3-b][1,5]-and-[3,2-b][1,5]-, and -[3,4-b][1,5]benzodiazepinones",J.C.S. Perkin I, pp. 937-941 (1978).

* cited by examiner

*Primary Examiner*—Brenda L Coleman
(74) *Attorney, Agent, or Firm*—Luedeka, Neely & Graham, P.C.

(57) ABSTRACT

The invention provides an Olanzapine pseudopolymoph Form E. The invention provides methods of preparing polymorphic Olanzapine Form E employing rapid crystallization and seeding. The invention provides methods of preparing anhydrous Olanzapine Form I from the Olanzapine Form E by step-wise drying.

27 Claims, 3 Drawing Sheets

POLYMORPH E OF OLANZAPINE AND PREPARATION OF ANHYDROUS NON-SOLVATED CRYSTALLINE POLYMORPHIC FORM I OF 2-METHYL-4(4-METHYL-1-PIPERAZINYL)-10H-THIENO[2,3-B][1,5] BENZODIAZEPINE (OLANZAPINE FORM I) FROM THE POLYMORPHIC OLANZAPINE FORM E

CROSS REFERENCE TO RELATED APPLICATIONS

Not Applicable

FIELD OF THE INVENTION

This application relates to methods of preparation of Olanzapine Form I and to a polymorphic Olanzapine Form E intermediate used in the preparation of Olanzapine Form I.

BACKGROUND OF THE INVENTION

Olanzapine Form I (2-methyl-4-(4-methyl-1-piperazinyl)-10H-thieno[2,3-b][1,5] benzodiazepine) having endotherm at 179° C. (weak) and 195° C. (strong), Form I, is used for pharmaceutical formulations. It is known that commercially available Olanzapine Form I prepared by methods of the prior art, for example, as disclosed in U.S. Pat. No. 5,229,382, exhibits color which is less than desirable for commercial pharmaceutical use especially since the color is found to change over time due to the exposure in air Investigators have disclosed, in U.S. Pat. No. 5,637,584, the solvated form of Olanzapine Form I as a mono (methylene chloride) solvate of Olanzapine. When the mono methylene solvate is crystallized from methylene chloride, Olanzapine Form I is generated.

Polymorphic Olanzapine Form I can also be prepared as a solvate of dimethylsulfoxide and water having different ratio (Olanzapine: DMSO:water) and then crystallization of this solvate form of crude Olanzapine using methylene chloride as a crystallization solvent to produce polymorphic form I of Olanzapine, as disclosed in WO 03/097650.

Others have disclosed a hydrate form of Olanzapine and the preparation of Olanzapine polymorph Form I from this hydrate and methods of converting Olanzapine form II to form I, as provided in WO 02/183390.

Recently preparation of Olanzapine Form I has focused on the generation of desired polymorphic Form I from the solvated Olanzapine using crystallization solvents.

Also, Olanzapine Form II is generated by prior art methods that include crystallization from ethyl acetate of the technical grade of Olanzapine Form I, as provided in U.S. Pat. No. 5,736,541.

The prior art, however, does not disclose a method for producing a stable Olanzapine Form I using rapid crystallization and seeding techniques to produce a novel polymorphic intermediate that is subjected to step-wise resulting in a pharmaceutically elegant and commercially useful amounts Olanzapine Form I having greater purity than that prepared by known methods.

SUMMARY OF THE INVENTION

One aspect of the present is a novel solvated polymorphic Form E of Olanzapine.

Another aspect of the present invention provides a process for preparing a novel solvated polymorphic Form E of Olanzapine.

Another aspect of the present invention provides a process for preparing a novel solvated polymorphic Form E of Olanzapine which can be employed in the production of a relatively pure form of Olanzapine Form I.

Another aspect of the invention is the preparation of an anhydrous non-solvated polymorphic Form I of 2-methyl-4-(4-methyl-1-piperazinyl)-10H-thieno[2,3-b][1,5] benzodiazepine known as Olanzapine, and a process of making such desired anhydrous polymorph I from a solvated polymorphic Form E of Olanzapine.

Another aspect of the invention is the preparation of pure non-solvated Olanzapine Form I by step-wise drying of novel polymorphic Olanzapine Form E produced by rapid crystallization in dichloromethane-methanol mixture with continuous seeding with ultra pure Olanzapine Form I.

Another aspect of the invention is the preparation of a substantially pure Olanzapine Form I by rapid crystallization in dichloromethane with continuous seeding with relatively small amounts of ultra pure Olanzapine Form I.

Another aspect of the invention provides methods for making non-solvated polymorphic Olanzapine Form I which can be applied in commercial scale with the formation of highly pure, pharmaceutically elegant polymorphic Olanzapine Form I.

DETAILED DESCRIPTION OF THE INVENTION

Figure 1:
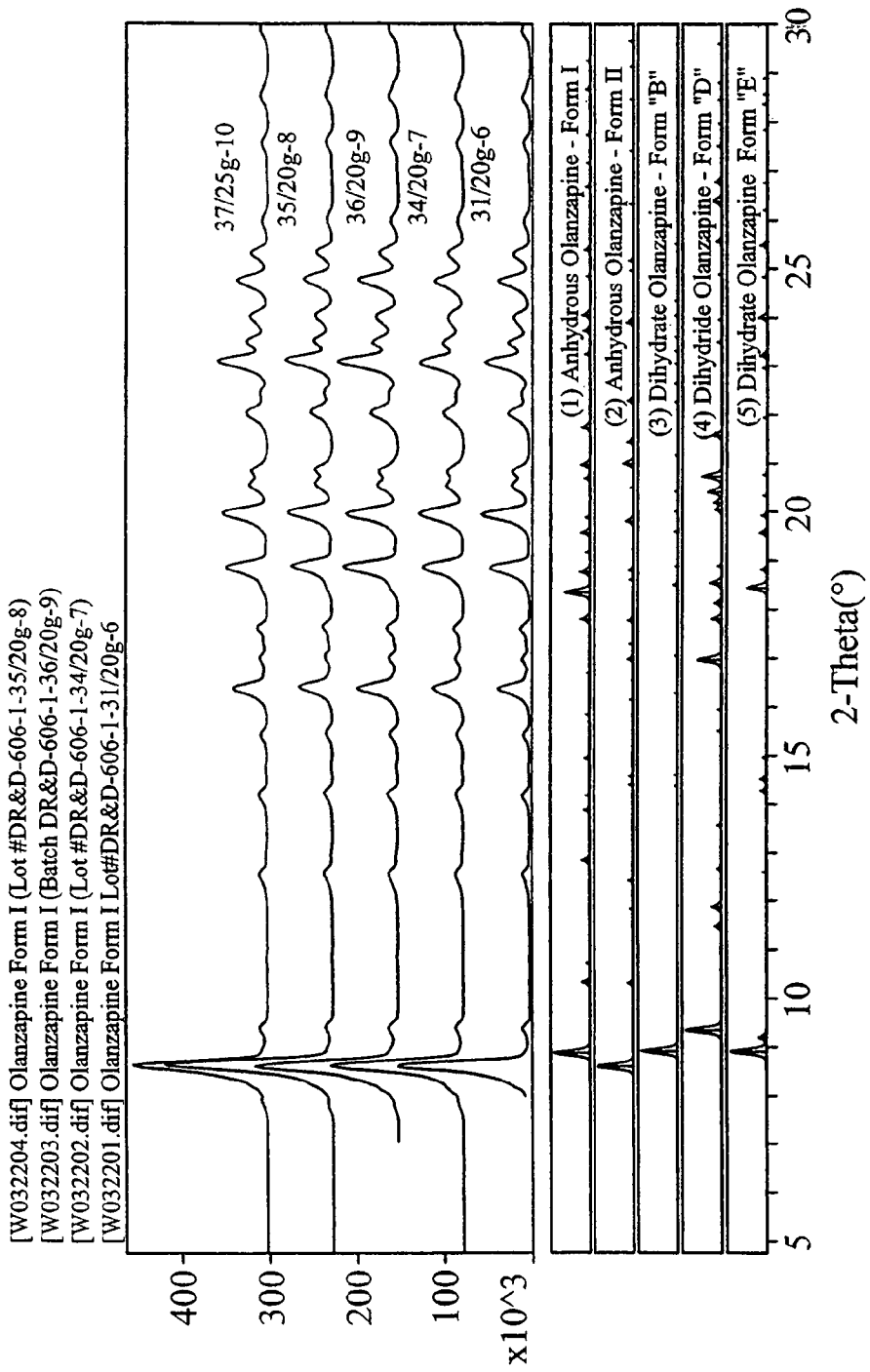
FIG. 1 is a comparison of XRD of five batches of air-dried five batches samples of new solvated Olanzapine poly-type E with the simulated XRD pattern of reported Olanzapine polymorphs in literatures.

One aspect of the invention employs the technique of using methanol-methylene chloride mixture with different ratio yields a new poly-type Olanzapine Form E which is different from the reported Olanzapine Form I, II, A, B, D and E. For example, five batches were prepared (10 g and 20 g) with 5% methanol-methylene chloride which shows new poly-type solvated Olanzapine Form E contains approximately average 5-7% methanol, 1.5-2% methylene chloride and 1-1.5% water when dried at room temperature (23° C.-24° C.) for 24 hours. GC of this air-dried samples show different contents of methanol and methylene chloride ratio (See, Table 4). FIG. 1 shows that all five batches of new polymorphic Olanzapine Form E are identical and do not match with any of the reported x-ray diffraction (XRD) in the literatures. All five samples appear to have undergone a phase transformation in which the Form I phase disappeared altogether and a new novel poly-type E appears as shown in FIG. 1.

If these air dried new solvated poly-type Olanzapine Form E materials are directly put in to the oven for drying at 40° C.-50° C., polymorph II is generated within the range about 8-10%. Consequently, a preferred method of the present invention employs a step-wise drying technique of the new poly-type solvated form E of Olanzapine, which when dried in step-wise fashion, has been found to form pure anhydrous Olanzapine Form I.

Solvated Form E of Olanzapine, which when dried in step-wise fashion forms pure anhydrous Olanzapine Form I. From FT-IR it is clear that the new solvated Form E is different from anhydrous Olanzapine Form I in the regions around 1029 $cm^{-1}$ and when the samples are dried sequentially, first at room temperature for approximately 24 hrs, then in rotatory evaporator under reduced pressure with different time profile (e.g. approximately 6 to 8 hrs) and ultimately at around 40° C. for approximately 1 to 2 hours, preferably about 1.4 to about 2 hours, the region at 1029 $cm^{-1}$ that is different from pure Form I decreases until it matches exactly with the Olanzapine Form I. At this stage the gas chromatography (GC) studies show that methanol and methylene chloride level varies between about 0.5-0.7% and about 0.01-0.05% (See, Table 4). Melting point (DSC) and TGA of these new solvated form show approximately 6.5 to 9% weight loss corresponding at around 130° C. which is the indication of loss of methanol bound water as evident from GC and Karl Fischer (KF) studies. (See, Table 3). The residual solvents that remain after drying at approximately 40° C. for around 1.4 hrs. as evident from GC (See, Table 4) are not bound solvents in all the five batches of samples are evident from TGA and DSC. XRD of all these dried batches of new polymorphic Form E are identical and matches with polymorphic Form I.

It was also found that during crystallization with methylene chloride if the crystallization was allowed to occur slowly at room temperature, solvate of Olanzapine was formed. XRD of this solvate shows major unknown phases with minor Form I but when this solvate is subjected to drying condition a major amount of Form I is generated with approximately 4 to 6% Form II.

The methods of the present invention employ rapid crystallization either with pure methylene chloride as a solvent or a mixture of methanol-methylene chloride or toluene-methylene chloride with a different ratio and a quick continuous seeding with ultra-pure Olanzapine Form I with vigorous stirring in less than 2 hours, preferably less than 1 hour and more preferably around 30 minutes or less crystallization time at 0° C. This rapid crystallization technique prevents the solvate formation of polymorph when using methylene chloride and the quality of the polymorphic purity will be very high. When using methylene chloride-methanol mixture the purity of Form I is very high, as the high solubility effect of methanol will not allow the crystallization to occur until the addition of a relatively small amount of ultra-pure Form I for seeding. For example, one illustrative aspect of the invention provides for continues seeding of approximately 20 to 25 mg of ultra-pure Olanzapine Form I per each 20 to 25 g. of product yielded.

One aspect of the present invention is directed to a stable polymorphic Form I of Olanzapine produced by using a mixture of methanol-methylene chloride (2%-20%) through rapid crystallization with seeding technique followed by step-wise drying techniques. Using this rapid crystallization technique with methylene chloride as a single solvent, a non-solvated anhydrous Olanzapine Form I can be generated with a substantially pure polymorphic state Another aspect of the present invention provides for a rapid crystallization either with pure methylene chloride as a solvent or a mixture of methanol-methylene chloride, or toluene-methylene chloride with a different ratio, and a quick continuous seeding with ultra-pure Olanzapine Form I with vigorous stirring in less than 30 minutes crystallization time at 0° C.

The rapid crystallization techniques of the present invention prevent the solvate formation of polymorphic Olanzapine Form II and the quality of the polymorphic purity of the Olanzapine Form I is very high. In the process employing a methylene chloride-methanol mixture, the purity of Olanzapine Form I is very high because the high solubility effect of methanol will not allow the crystallization to occur until the addition of ultra-pure Olanzapine Form I during seeding.

In another aspect of the invention activated charcoal (pH 7-8, Norrit, 4-8 mesh size) is employed at the end of the process to produce high quality polymorphic Olanzapine Form I with the elimination of coloring impurity in the Olanzapine Form I, which generally is formed during basic aqueous sodium hydroxide treatment and exposure to air. If charcoal is not used in the methods of the present invention, the color impurity can be washed away to some extent during filtration with chilled methylene chloride or methanol-methylene chloride mixture and polymorphic impurity content does not change.

The present invention employing rapid crystallization technique to prepare polymorphic Olanzapine Form I in methylene chloride or methanol-methylene chloride mixture not only shows an endotherm peak at about 195 in DSC of all the batches produced under identical conditions but also shows a typical X-ray powder diffraction pattern that matches well with the representative standard Olanzapine Form I after application of proper drying technique.

In another aspect of this invention the new poly-type Olanzapine Form E generated with rapid crystallization in methylene chloride-methanol along with step-wise drying techniques produces non-solvated anhydrous Form I of 2-methyl-4-(4-methyl-1-piperazinyl)-10H-thieno[2,3-b][1,5] benzodiazepine which is stable enough to be used commercially in pharmaceutical formulations. No color change has been found to occur during the exposure of this material at room temperature for at least 3 months.

In another aspect of this invention, the solvated new poly-type Olanzapine Form E of 2-methyl-4-(4-methyl-1-piperazinyl)-10H-thieno[2,3-b][1,5] benzodiazepine to assure reproducibility and uniformity of the product which can be applied in the production scale. The new poly-type Olanzapine Form E is prepared using a convenient, efficient and ecologically acceptable process, which can be exploited in the final step during the synthesis of the drug.

The new poly-type E is stable at room temperature but when subjected to step-wise drying techniques results in substantially pure Olanzapine Form I.

In one example of the broader methods of preparing the Olanzapine Form E according to the invention, the technical grade 4-amino-2-methyl-10H-thieno [2,3-b][1,5] benzodiazepine HCl, and N-methylpiperazine is dissolved in anhydrous dimethyl sulfoxide and heated at about 112° C.-115° C. for approximately 16 hours. The reacting solution is treated with a mixture of dichloromethane, water and methanol. After separating the organic phase the aqueous phase is again extracted with dichloromethane and the combined organic solvents are extracted with acetic acid, basified at specific low temperature and again extracted with methanolic-dichloromethane (5:95) mixture. The mixture is washed with warm water (around 30° C.) and dried over anhydrous sodium sulfate. After drying, methanolic-dichloromethane mixture was evaporated under reduced pressure to a critical volume (approximately ⅓ of the original volume) and new poly-type Olanzapine Form E crystallized out by seeding with ultra-pure Olanzapine polymorph Form I.

The polymorphic Olanzapine Form E prepared by this rapid crystallization technique with the combination of solvents of the present invention has same physical and chemical property as Olanzapine polymorph Form I when converted to anhydrous form by step-wise drying techniques. Using this technique undesired polymorphic Olanzapine Form II can be limited as low as approximately 0.4% or can be eliminated. The novel techniques of present invention provide pharmaceutically elegant and desirable properties needed for a drug to be administered to psychotic patients, and has satisfactory color and thermal stability for solid dosage form and is substantially free of undesired other polymorphs and devoid of stoichiometric solvating agents such as water and organic solvents.

Process for Producing Olanzapine I

The present invention is directed to a process for producing Olanzapine form I, which comprises reacting N-methylpiperazine and a compound of formula in which Q is a group capable of being split off.

II:

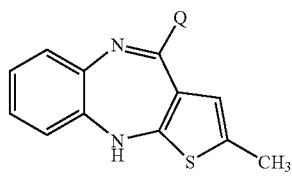

The radical Q can, for example, be an amino group or a mono- or dialkyl-substituted amino group (each alkyl substituent containing 1 to 4 carbon atoms), hydroxyl, thiol, or an alkoxy, alkylthio or alkylsulphonyl group containing 1 to 4 carbon atoms, such as methoxy or methylthio, or a halogen, such as chlorine. Preferably, Q is amino (—$NH_2$), hydroxyl or thiol, amino being preferred. The amidine of formula (II), where Q is —$NH_2$, can be in salt form, for example a salt of a mineral acid such as the hydrochloride.

The reaction is carried out in the presence of an aprotic high boiling solvent, preferably anhydrous dimethyl sulfoxide, at a temperature of from about 50° C. to around 200° C., or from about 90° C. to about 130° C. or in a range from approximately 115° C. to approximately 120° C., or around 110° C. The resulting Olanzapine is purified in an acidic medium followed by extraction with organic solvents. The acidic medium for the purification step can be prepared with an organic acid, preferably about 40-60% acetic acid. The resulting mixture is then basified under cold conditions, 0° C. to 10° C., preferably to a pH of about 7.5-8.5 using an inorganic base such as sodium hydroxide, potassium hydroxide or lithium hydroxide. Sodium hydroxide is the preferred agent. More preferably about 30-60% aqueous sodium hydroxide is used. After the desired pH is obtained, the mixture is subjected to extraction using a low boiling organic solvent such as methanolic-dichloromethane mixture, diethylether, dichloroethane, chloroform, isopropanol-methylenechloride mixture, dichloromethane-methanol, dichloromethane, methanol-chloroform mixture, ethyl acetate or other low polar ketonic solvents. Preferably the solvent is dichloromethane or methanolic-dichloromethane or isopropanol-dichloromethane.

After extraction with mixture of organic solvent, the organic solvent mixture was evaporated under reduced pressure to a critical volume. A critical step lies in the use of seeding technique with time profile for crystallization and separate out form I Olanzapine. Seeding with rapid crystallization technique as used herein generally refers to a time-bound state of the process that results from a critical volume of mixture of solvent with stochiometric ratio of mixture of solvents. Rapid crystallization generally refers to over less than approximately two hours, preferably about one hour and most preferably over about thirty minutes or less.

Examples of mixture of solvents include methanol-dichloromethane, dichloromethane-toluene, dichloromethane-methyl ethyl ketone, dichloromethane-acetonitrile-methanol, mixture of n-propanol-dichloromethane, isopropanol-dichloromethane-methanol or dichloromethane as a single solvent. Combination of methanol-dichloromethane with different proportion is most preferred.

In one aspect of the present invention, prior to extraction, the solution is made basic to a pH of about 7.5-8.5 at approximately 0° C.-10° C. using aqueous sodium hydroxide. With the solution in this basic state, extraction is done with mixture of methanol and dichloromethane or dichloromethane. Each extraction step produces an aqueous phase and a methanolic-dichloromethane or dichloromethane phase. After washings and extraction, the methanolic-dichloromethane or dichloromethane is reduced to a critical volume (generally about ⅓ of the total volume) by rotary evaporation. Pure anhydrous non-solvated Olanzapine Form I can be crystallized rapidly with stirring from mixture of methanol and dichloromethane or dichloromethane solvent by seeding with ultra-pure Olanzapine Form I.

In one aspect of the present invention, prior to extraction, the solution is made basic to a pH of about 7.5-8.5 using aqueous sodium hydroxide. With the solution in this basic state, extraction is done with mixture of methanol and dichloromethane or dichloromethane. Each extraction step produces an aqueous phase and a methanolic-dichloromethane phase. The combined methanolic-dichloromethane mixture is treated with basic activated charcoal. After filtration over celite, the methanolic-dichloromethane mixture is reduced to a critical volume (e.g. about ⅓ of the total volume) by rotary evaporation. Pure anhydrous non-solvated Olanzapine form I can be crystallized rapidly from the mixture of methanol and dichloromethane solvent by seeding with ultra-pure Olanzapine form I. The carbon treatment does not change the polymorphic status of the Olanzapine polymorph I. Charcoal treated material results free flowing solid which is helpful in solid dosage form. These processes have high degree of reproducibility and can be scaled up to production scale.

In another aspect of the present invention, the reaction mixture is extracted using a low boiling point solvent with good solubility, preferably dichloromethane, after basification e.g.; to around pH 7.5-8.5, as discussed above and treated the organic phase with basic charcoal. After filtration over celite and evaporation dichloromethane to a critical volume, the rapid crystallization technique by seeding will provide a non-solvated anhydrous Olanzapine Form I. Here the charcoal treatment also generates the same quality material as described above and has very high degree of reproducibility. Irrespective of methylene chloride or methanol-methylene chloride mixture, the technique of rapid crystallization yielded substantially pure nonsolvated anhydrous polymorphic Olanzapine Form I which are confirmed by FT-IR, GC, KF, TGA, DSC and XRD.

The invention will now be illustrated by the following examples, which are merely illustrative and not intended to limit the scope of the present invention.

EXAMPLE 1

Preparation of Olanzapine Form I from Pseudopolymorph Olanzapine Form E by Rapid Crystallization in Methanol-Methylene Chloride by Seeding

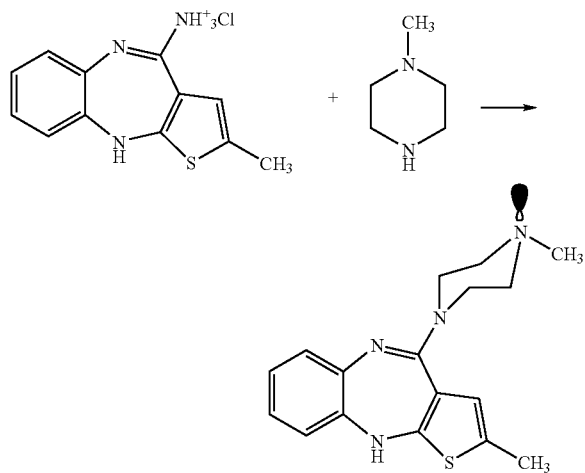

A three necked flask, fitted with nitrogen gas inlet, water condenser with calcium chloride guard tube, is charged with 4-amino-2-methyl-10H-theino[2,3-b][1,5] benzodiazepine HCl (20.0 g, 0.0752 mol), 1-methylpiperazine (54.0 ml, 0.45 mol, 99.0%, Aldrich Chemicals, USA) and anhydrous dimethyl sulfoxide (120.0 ml, Aldrich Chemicals, USA, water<0.1%). The reaction mixture is stirred at 112-115° C. (Oil bath temperature around 115° C.) for approximately 16 hours under continuous flow of nitrogen to drive away the ammonia gas generated during the reaction. Reaction is monitored by HPLC and it is found that within 16 hours approximately 97% product is formed. The reaction mixture is cooled to room temperature (e.g. around 24-25° C.) and added slowly to a mixture of dichloromethane: water: methanol (approximately 760:760:75 ml). After addition, the reaction mixture is stirred for around 30 minutes at room temperature. The resulting mixture is yellowish hazy with a dark brown organic layer settled at the bottom of the flask. The dark brown colored organic layer is separated from the aqueous hazy phase.

After separating the organic layer, the aqueous hazy phase is again extracted with dichloromethane (1×200.0 ml). The combined organic phases (total volume approximately 1035.0 ml) are extracted twice with 50% aqueous acetic acid solution (1×450 ml, 1×150.0 ml). A dark orange color acetic acid layer is separated. The pH of the acetic acid solution is found to be around 3.0-3.5 when tested by litmus paper. Combined aqueous acetic acid solution is basified, to pH 7.5-8.5, using slow drop wise addition of 40% aqueous sodium hydroxide solution under cold conditions (e.g. around 0-10° C.). The temperature preferably should be maintained in the mentioned range otherwise coloring impurity may generate to contaminate with the pure polymorph. After attaining the desired pH of the solution, approximately 400 ml dichloromethane and approximately 20 mL methanol mixture is added and stirred. The content is transferred to a separating funnel and is vigorously shaken.

The methanolic-dichloromethane layer is separated and the aqueous phase is again extracted with same composition of methanolic-dichloromethane (1×100 ml). The combined methanol-dichloromethane extracts are washed with cold saturated sodium chloride solution (1×30.0 ml) and dried over anhydrous sodium sulfate. Removal of solvent on a rotary evaporator with a water bath temperature of around 45° C., gives a dark orange brown viscous liquid. Volume of the orange brown liquid is about 50 mL. The hot solution is removed from the water bath and cooled in an ice bath with stirring. Within about 2 to 3 minutes, the solution is quickly seeded with previously prepared ultra pure Olanzapine Form I, as determined by X-Ray and IR analyses, with stirring. Stirring is continued for about 30-35 minutes. The yellowish solid obtained in the solution is filtered off, washed with approximately 8-10 ml of chilled 5% methanol-dichloromethane and dried on a vacuum pump for about an hour to give approximately 16.2 g (72% yield) of new poly-morph Olanzapine Form E, as shown in FIG. 1.

The solid obtained is crushed to a fine powder and air-dried to remove traces of methanol-dichloromethane. Karl Fisher analysis of air-dried material indicates 8000 ppm water. The material is dried in a stepwise fashion, resulting in Olanzapine Form I, and ultimately dried in an oven at around 40° C. for approximately 1.4 hours and analyzed for water again (approximately 670 ppm water). The weight of the Olanzapine Form I product is 3.95 g (71% yield), HPLC purity=99.93%, polymorphic purity is 99% as 1% polymorph Olanzapine Form II is observed by X-ray.

EXAMPLE 2

Preparation of Olanzapine form I From Pseudopolymorph Olanzapine Form E by Rapid Crystallization in Methanol-Methylene Chloride by Seeding along with Carbon Treatment A three necked flask, fitted with nitrogen gas inlet, water condenser with calcium chloride guard tube, is charged with 4-amino-2-methyl-10H-theino[2,3-b][1,5] benzodiazepine HCl (20.0 g, 0.0752 mol), 1-methylpiperazine (54.0 ml, 0.45 mol, 99.0%, Aldrich Chemicals, USA) and anhydrous dimethyl sulfoxide (120.0 ml, Aldrich Chemicals, USA, water<0.1%). The reaction mixture is stirred at approximately 112-115° C. (Oil bath temperature around 115° C.) for approximately 16 hours under continuous flow of nitrogen to drive away the ammonia gas generated during the reaction. Reaction is monitored by HPLC and it is found that within 16 hours 97% product is formed. The reaction the mixture is cooled to room temperature (e.g. around 24-25° C.) and added slowly to a mixture of dichloromethane: water:methanol (760:760:75 ml). After addition, the reaction mixture is stirred for about 30 minutes at or near room temperature. The resulting mixture is yellowish hazy with a dark brown organic layer settled at the bottom of the flask. The dark brown colored organic layer is separated from the aqueous hazy phase.

After separating the organic layer, the aqueous hazy phase is again extracted with dichloromethane (1×200.0 ml). The combined organic phases (total volume approximately 1035.0 ml) are extracted twice with 50% aqueous acetic acid solution (1×450 ml, 1×150.0 ml). A dark orange color acetic acid layer is separated. The pH of the acetic acid solution is found to be around 3.0-3.5 when tested by litmus paper. Combined aqueous acetic acid solution is basified, to around pH 7.5-8.5, using slow drop wise addition of 40% aqueous sodium hydroxide solution under cold conditions (e.g. around 0-10° C.). The temperature preferably should be maintained in the mentioned range otherwise coloring impurity may generate to contaminate with the pure polymorph). After attaining the desired pH of the solution, approximately 400 ml dichloromethane and 20 mL methanol is added and stirred. The content is transferred to a separating funnel and is vigorously shaken. The methanolic-dichloromethane layer is separated and the aqueous phase is again extracted with same composition of methanolic-dichloromethane (1×100 ml).

The methanol-dichloromethane extract is treated with approximately 1.0 g charcoal (5%, Aldrich Chemical, pH water extract 6.0-7.0) and warm the solution with stirring. After stirring for approximately 30 minutes, it was filtered-off through celite and washed the celite with 15-20 mL methanol-dichloromethane mixture. The combined methanol-dichloromethane extracts are washed with cold saturated sodium chloride solution (1×30.0 ml) and dried over anhydrous sodium sulfate. Removal of solvent on a rotary evaporator with a water bath temperature of around 45° C., gives a dark orange brown viscous liquid. Volume of the orange brown liquid is about 50 mL. The hot solution is removed from the water bath and cooled in an ice bath with stirring. Within approximately 2 to 3 minutes, the solution is quickly seeded with previously prepared ultra pure Olanzapine Form I, as determined by X-Ray and IR analyses, with stirring. Stirring is continued for around 30 to 35 minutes.

The yellowish solid obtained in the solution is filtered off, washed with 8-10 ml of chilled 5% methanol-dichloromethane and dried on a vacuum pump for about an hour to give approximately 16.2 g (72% yield) of Olanzapine Form E. The solid obtained is crushed to a fine powder and air-dried to remove traces of methanol-dichloromethane. Karl Fisher analysis of air-dried material indicates 800 ppm water. The material is subjected to step wise drying conditions and ultimately dried in an oven around 40° C. for approximately 1.4 hours, resulting in Olanzapine Form I, and analyzed for water again (approximately 600 ppm water). The weight of the resulting Olanzapine Form I product is 3.890 g (approximately 71% yield), HPLC purity=99.99%, polymorphic purity is 99.65% as 0.35% polymorph II is observed by X-ray.

EXAMPLE 3

Preparation of Olanzapine Form I by Rapid Crystallization in Methylene Chloride by Continuous Seeding A three necked flask, fitted with nitrogen gas inlet, water condenser with calcium chloride guard tube, is charged with 4-amino-2-methyl-10H-theino[2,3-b][1,5] benzodiazepine HCl (20.0 g, 0.0752 mol), 1-methylpiperazine (54.0 ml, 0.45 mol, 99.0%, Aldrich Chemicals, USA) and anhydrous dimethyl sulfoxide (120.0 ml, Aldrich Chemicals, USA, water<0.1%). The reaction mixture is stirred at around 112-115° C. (Oil bath temperature around 115° C.) for approximately 16 hours under continuous flow of nitrogen to drive away the ammonia gas generated during the reaction. Reaction is monitored by HPLC and it is found that within approximately 16 hours around 97% product is formed. The reaction the mixture is cooled to room temperature (e.g. around 24-25° C.) and added slowly to a mixture of dichloromethane:water:methanol (760:760:75 ml). After addition, the reaction mixture is stirred for about 30 minutes at or near room temperature. The resulting mixture is yellowish hazy with a dark brown organic layer settled at the bottom of the flask. The dark brown colored organic layer is separated from the aqueous hazy phase.

After separating the organic layer, the aqueous hazy phase is again extracted with dichloromethane (1×200.0 ml). The combined organic phases (total volume approximately 1035.0 ml) are extracted twice with 50% aqueous acetic acid solution (1×450 ml, 1×150.0 ml). A dark orange color acetic acid layer is separated. The pH of the acetic acid solution is found to be around 3.0-3.5 when tested by litmus paper. Combined aqueous acetic acid solution is basified, to pH of approximately 7.5 to 8.5, using slow drop wise addition of 40% aqueous sodium hydroxide solution under cold conditions (e.g. around 0-10° C.). The temperature preferably should be maintained at the mentioned range otherwise coloring impurity may generate to contaminate with the pure polymorph). After attaining the desired pH of the solution, approximately 400 ml dichloromethane is added and stirred.

The content is transferred to a separating funnel and is vigorously shaken. The dichloromethane layer is separated and the aqueous phase is again extracted with same composition of dichloromethane (1×100 ml). The combined dichloromethane extracts are washed with cold saturated sodium chloride solution (1×30.0 ml) and dried over anhydrous sodium sulfate. Removal of solvent on a rotary evaporator with a water bath temperature of around 45° C., gives a dark orange brown viscous liquid. Volume of the orange brown liquid is about 50 mL. The hot solution is removed from the water bath and cooled in an ice bath with stirring. Within approximately 2 to 3 minutes, the solution is quickly seeded with previously prepared ultra pure Olanzapine Form I, as determined by X-Ray and IR analyses, with stirring. Stirring is continued for about 30 to 35 minutes. The yellowish solid obtained in the solution is filtered off, washed with approximately 8-10 ml of chilled 5% dichloromethane and dried on a vacuum pump for about an hour to give around 16.5 g (72.4% yield). The solid obtained is crushed to a fine powder and air-dried to remove traces of dichloromethane. Karl Fisher analysis of air-dried material indicates 700 ppm water. The material is subjected to step wise drying and ultimately dried in an oven at around 65° C. for approximately 1.5 to 2.0 hours and analyzed for water again (approximately 200 ppm water). XRD shows the solid is Olanzapine Form I. The weight of the title product is 4.80 g (82% yield), HPLC purity=99.93%, polymorphic purity is 99% as 1% polymorph II is observed by X-ray (FIG. 2).

EXAMPLE 4

Preparation of Olanzapine Form I by Rapid Crystallization in Methylene Chloride by Seeding Along with Carbon Treatment A three necked flask, fitted with nitrogen gas inlet, water condenser with calcium chloride guard tube, is charged with 4-amino-2-methyl-10H-theino[2,3-b][1,5] benzodiazepine HCl (20.0 g, 0.0752 mol), 1-methylpiperazine (54.0 ml, 0.45 mol, 99.0%, Aldrich Chemicals, USA) and anhydrous dimethyl sulfoxide (120.0 ml, Aldrich Chemicals, USA, water<0.1%). The reaction mixture is stirred at around 112 to 115° C. (Oil bath temperature about 115° C.) for approximately 16 hours under continuous flow of nitrogen to drive away the ammonia gas generated during the reaction. Reaction is monitored by HPLC and it is found that within about 16 hours approximately 97% product is formed. The reaction the mixture is cooled to room temperature (e.g. around 24-25° C.) and added slowly to a mixture of dichloromethane:water:

methanol (approximately 760:760:75 ml). After addition, the reaction mixture is stirred for around 30 minutes at or near room temperature. The resulting mixture is yellowish hazy with a dark brown organic layer settled at the bottom of the flask. The dark brown colored organic layer is separated from the aqueous hazy phase.

After separating the organic layer, the aqueous hazy phase is again extracted with dichloromethane (1×200.0 ml). The combined organic phases (total volume approximately 1035.0 ml) are extracted twice with 50% aqueous acetic acid solution (1×450 ml, 1×150.0 ml). A dark orange color acetic acid layer is separated. The pH of the acetic acid solution is found to be around 3.0 to 3.5 when tested by litmus paper. Combined aqueous acetic acid solution is basified, to pH around 7.5 to 8.5, using drop wise addition of 40% aqueous sodium hydroxide solution under cold conditions (e.g., around 0-10° C.). The temperature preferably should be maintained at the mentioned range otherwise coloring impurity may generate to contaminate with the pure polymorph.

After attaining the desired pH of the solution, 400 ml dichloromethane is added and stirred. The content is transferred to a separating funnel and is vigorously shaken. The dichloromethane layer is separated and the aqueous phase is again extracted with dichloromethane (1×100 ml). The combined dichloromethane extracts are washed with cold saturated sodium chloride solution (1×30.0 ml) and dried over anhydrous sodium sulfate. The dichloromethane extract is treated with approximately 1.0 g charcoal (5%, Aldrich Chemical, pH water extract 7.0-8.0) and warm the solution with stirring. After stirring for around 30 minutes, it was filtered-off through celite and washed the celite with approximately 15-20 mL dichloromethane mixture. Removal of solvent on a rotary evaporator with a water bath temperature of around 45° C., gives a dark orange brown viscous liquid. Volume of the orange brown liquid is about 50 mL.

The hot solution is removed from the water bath and cooled in an ice bath with stirring. Within approximately 2 to 3 minutes, the solution is quickly seeded with previously prepared ultra pure Olanzapine Form I, as determined by X-Ray and IR analyses, with stirring. Stirring is continued for about 30-35 minutes. The yellowish solid obtained in the solution is filtered off, washed with 8-10 ml of chilled 5% dichloromethane and dried on a vacuum pump for about an hour to give 16.5 g (72.4% yield) of Olanzapine Form I. The solid obtained is crushed to a fine powder and air dried to remove traces of dichloromethane. Karl Fisher analysis of air dried material indicates 500 ppm water. The material is subjected to step wise drying and ultimately dried in an oven at around 40° C. for approximately 1.4 hours and analyzed for water again (around 200 ppm water). The weight of the title product is 4.80 g (82% yield), HPLC purity=99.93%, polymorphic purity is 99.5% as 0.5% polymorph II is observed by X-ray (FIG. 2).

EXAMPLE 5

Analysis of Samples

Olanzapine Form I prepared according to Example 1, is analyzed by X-ray, IR and DSC and found to conform to a commercially available Olanzapine Form I reference standard. DSC of Olanzapine form I prepared according to the present invention, shows an endotherm peak at about 195° C.

The X-ray powder diffractometry (XRD) Study of Olanzapine Form I and Form II is done in the following manner. The powder of polymorph is filled in an aluminum holder and exposed to CuKα radiation (40 kV×30 mA) in a wide range X-ray powder diffractometer (Model D5005, Siemens). The instrument is operated in the step-scan mode, in increments of about 0.02° 2θ. The angular range is around 5 to 50° 2θ and counts are accumulated for approximately 1 second at each step. A typical x-ray diffraction pattern for Olanzapine Form I is as follows wherein d represents the interplanar spacing and $I/I_0$ represents the typical relative intensities. In the following tables (Olanzapine Form I and Form II) only those peaks whose relative intensity $I/I_0$ is equal or greater than 10% are listed.

| d | $I/I_0$ |
|---|---|
| 9.9463 | 100.00 |
| 8.5579 | 15.18 |
| 6.8862 | 14.73 |
| 4.8333 | 68.37 |
| 4.7255 | 21.88 |
| 4.533 | 17.83 |
| 4.2346 | 18.88 |
| 4.855 | 17.29 |
| 3.7489 | 10.64 |
| 3.6983 | 14.65 |

A typical example of an x-ray diffraction pattern for Form II is as follows wherein d represents the interplanar spacing and $I/I_0$ (>10%) represents the typical relative intensities: Standard Polymorph form II was obtained from Neuland, India.

| d | $I/I_0$ |
|---|---|
| 10.2689 | 100.00 |
| 4.4787 | 14.72 |
| 4.2294 | 23.19 |
| 4.141 | 11.28 |
| 3.7206 | 14.04 |

FIG. 1 illustrates the typical XRD pattern of solvated (methanol-dichloromethane) new poly-type E dried at room temperature (around 25° C. to 26° C.) for about 24 hours. All the five batches are identical in XRD pattern. FIG. 1 also provides a comparison of XRD of the air-dried batch samples of new solvated Olanzapine poly-type E with the simulated XRD pattern of reported Olanzapine Forms I and II polymorphs as provided in literatures. The XRD patterns of the five batches are different from any of the reported poly-type in the literatures.

Figure 2A:
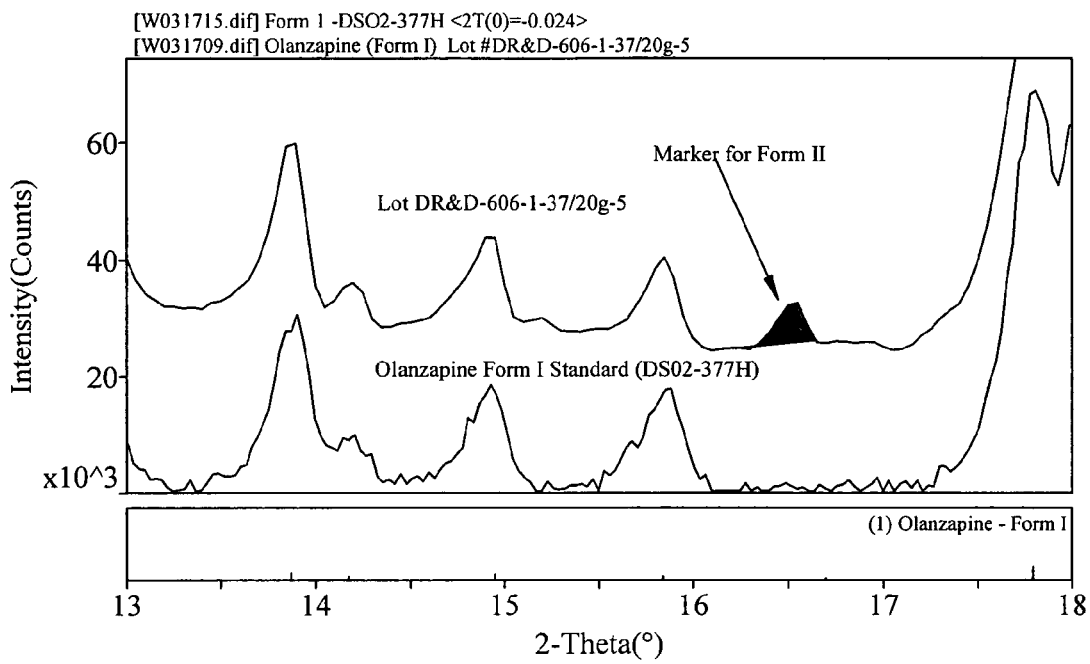
FIG. 2A illustrates the selection of regions for Form II marker and standardization for quantification of Olanzapine Form II in Form I by standard addition method.
Figure 2B:
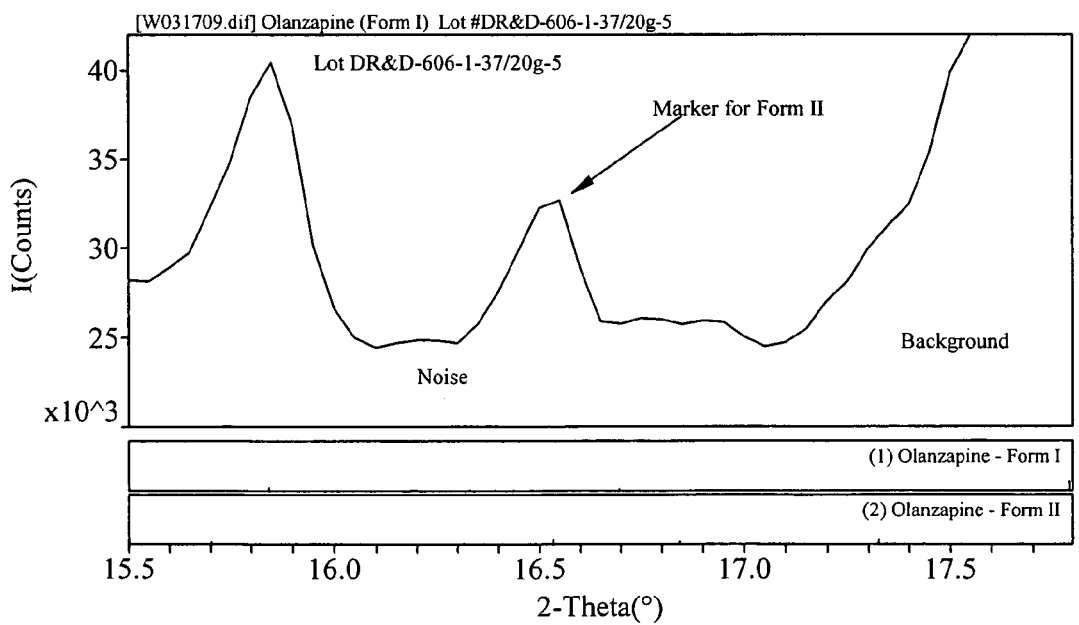
FIG. 2B illustrates the selection of regions for Form II marker and standardization for quantification of Olanzapine Form II in Form I by standard addition method.
Figure 2C:
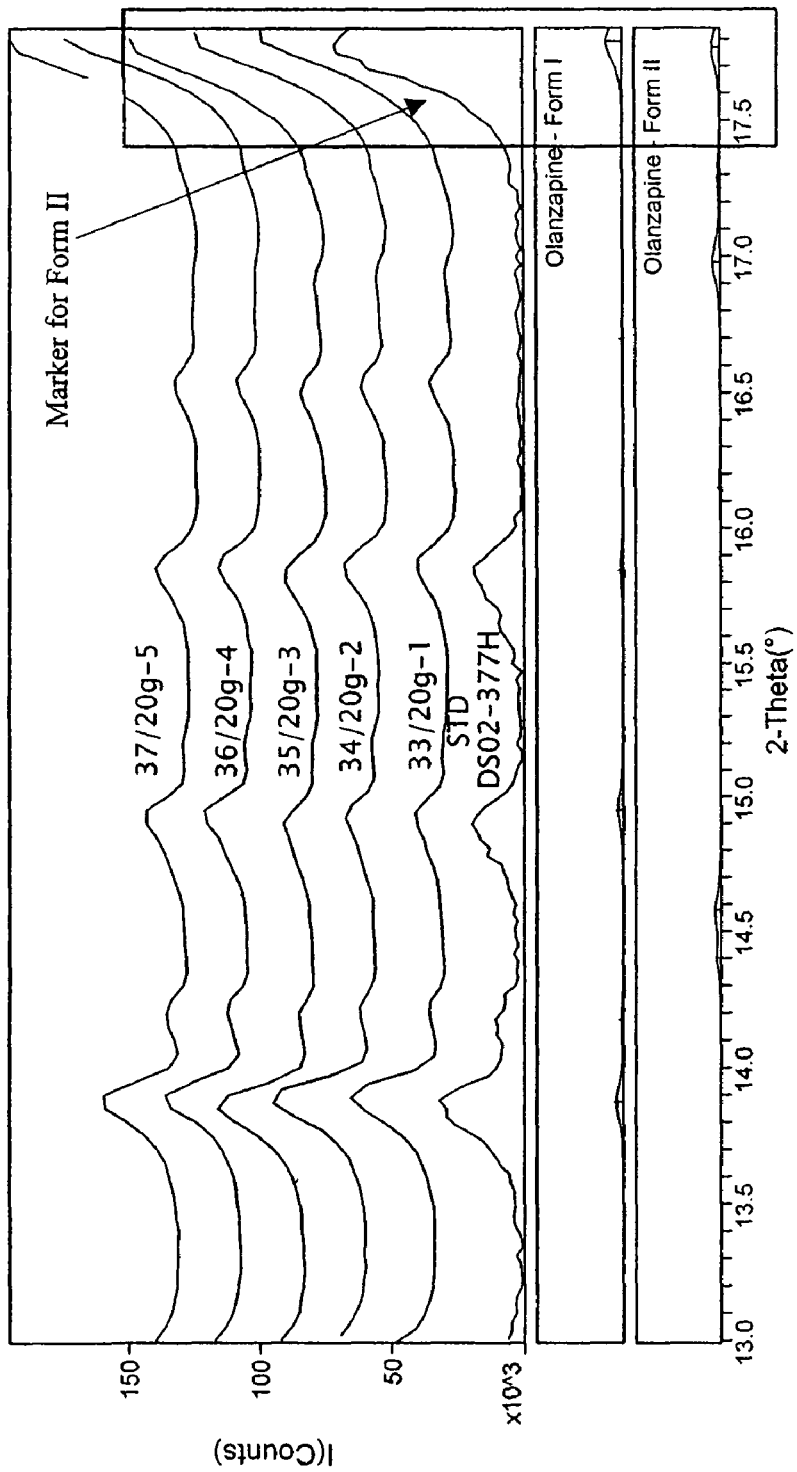
FIG. 2C illustrates the relative amounts of Olanzapine Form II in five batches of dried samples of Olanzapine Form I prepared by a method of the present invention.

FIGS. 2A and 2B show the selection of regions for Form II marker and standardization for quantification of Olanzapine Form II in Form I by standard addition method. FIG. 2C shows five batches of dried samples dried step wise and finally at around 40° C. for 1.4 hrs. The upper two traces illustrate with carbon treatment and lower three traces without carbon treatment. The bottom is the standard Olanzapine Form II. Marker of Olanzapine Form II in all the five batches of samples highlighted from top to bottom show the weight percentage of Form II in Form I as about 0.39%, 0.54%, 0.94%, 1.03% and 1.05% respectively calculated on the basis of standard addition method.

The following Table 1 is a comparison of XRD of the solvated Olanzapine Form E with the mono-methylene chloride solvate which clearly shows XRD pattern of new poly-type E is completely different from reported solvate of mono-methylene chloride as reported in U.S. Pat. No. 5,637,584.

TABLE 1

| New Solvated Polymorph E | | U.S. Pat. No. 5,637,584 | |
|---|---|---|---|
| "d" spacing | Intensity (%) | "d" spacing | Intensity (%) |
| 11.1259 | 4 | | |
| 10.2393 | 100 | 10.3721 | |
| 9.3935 | 6 | 9.4579 | |
| 7.0421 | 6 | 8.0541 | |
| 6.8319 | 1 | 7.4887 | |
| 6.2405 | 6 | 6.7033 | |
| 5.9907 | 1 | 6.5341 | |
| 5.7448 | 5 | 5.6880 | |
| 5.4101 | 26 | 5.5067 | |
| 5.2117 | 5 | 5.2097 | |
| 5.1037 | 3 | 4.7905 | |
| 5.0277 | 7 | 4.5342 | |
| 4.8060 | 5 | 4.3932 | |
| 4.7016 | 31 | 4.1624 | |
| 4.4427 | 33 | 4.0157 | |
| 4.3203 | 14 | 3.9705 | |
| 4.2594 | 12 | 3.8522 | |
| 4.0299 | 16 | 3.7535 | |
| 3.9605 | 6 | 3.6804 | |
| 3.8490 | 33 | 3.6335 | |
| 3.7855 | 14 | 3.5198 | |
| 3.7020 | 12 | 3.4890 | |
| 3.5956 | 21 | 3.4399 | |
| 3.5160 | 13 | 3.3491 | |
| 3.4282 | 5 | 3.2431 | |
| 3.2901 | 1 | 3.1714 | |
| 3.2339 | 5 | 3.1075 | |
| 3.1271 | 6 | 3.0437 | |
| 2.9886 | 6 | 2.9476 | |
| 2.9117 | 3 | 2.8872 | |
| 2.7893 | 4 | 2.8466 | |
| 2.7394 | 5 | 2.7906 | |
| 2.6566 | 2 | 2.7239 | |
| 2.6384 | 1 | 2.6859 | |
| 2.6051 | 2 | 2.6116 | |
| 2.5426 | 1 | 2.5729 | |
| 2.5034 | 6 | | |
| 2.4500 | 1 | | |
| 2.4136 | 1 | | |
| 2.3482 | 2 | | |
| 2.3033 | 1 | | |
| 2.2845 | 1 | | |

EXAMPLE 6

Identification and Polymorphic Purity of Olanzapine Form I Prepared According to Example 1

Identification and polymorphic purity of Olanzapine Form I prepared according to Example 1 has been investigated by FT-IR. FT-IR can distinguish clearly the presence either polymorphic Olanzapine Form I or polymorphic Olanzapine Form II in the mixture. A peak to peak comparison of the FT-IR for both forms clearly show characteristic regions where one of the Forms does not show any peak while other Form does (Table 2).

Expanded FT-IR spectrum shows that Form II's peak region at 887 cm$^{-1}$ is missing in Form I and well separated from the closest peak of Form I at 903 cm$^{-1}$. In a standard addition method using FT-IR, a contamination level of minimum 3% of Form II in Form I can be detected and quantified. Expanded FT-IR spectrum shows Form II at 3% level and 5% level in Form I. Reference Standard Polymorph Form I was obtained from Dr. Reddy's Laboratories and Form II from Neuland Laboratories, India.

FT-IR of Olanzapine Polymorphic Form I and Form II

TABLE 2

| Form I (v, cm$^{-1}$) | Form II (v, cm$^{-1}$) |
|---|---|
| 661 | — |
| — | 671 |
| — | 746 |
| 758 | — |
| 779, doublet | 785, singlet |
| 832 | — |
| — | 886 |
| 903 | — |
| — | 941 |
| — | 964 |
| 970 | — |
| 1005 | — |
| — | 1009 |
| — | 1102 |
| — | 1259 |
| — | 1330 |
| 1344, single | 1344, doublet |
| — | 1369 |
| 1526 | — |

As the process is carried out in aqueous sodium hydroxide, the sulfated ash value in the polymorphic Olanzapine Form I will have great impact on HPLC assay and purity. It has been found that washing with warm water lowers the ash content value to meet the specification. Step wise drying material of five batches were subjected to ROI (residue on ignition), KF DSC and HPLC which are furnished in Table 3.

TABLE 3

Water content by Karl Fisher, Melting Point (DSC), % Purity (HPLC) and Sulfated Ash Content by ROI (Residue on Ignition) of dried Olanzapine Form I.

| Olanzapine Form I Lot# | Water content % (KF) | Melting Point ° C. (DSC) | % HPLC Purity | Ash Content % |
|---|---|---|---|---|
| DR&D-1-33-20g | 0.0623 | 179.0, 195 | 99.90 | 0.00 |
| DR&D-1-34-20g | 0.0936 | 179.0, 195 | 99.95 | 0.02 |
| DR&D-1-35-20g | 0.0523 | 179.0, 195 | 99.94 | 0.03 |
| DR&D-1-36-20g | 0.0664 | 179.0, 195 | 99.95 | 0.02 |
| DR&D-1-37-25g | 0.0547 | 179.0, 195 | 99.95 | 0.06 |

Table 4 shows the GC of organic volatile impurity of five batches at room temperature drying and step-wise drying in ppm.

TABLE 4

Organic Volatile Impurities Rapidly Crystallized Olanzapine Form I(Residual Solvents) by Gas Chromatography

| | Air Drying (Over Night) | | Air Dried, Rota Dried, about 40° C. in Oven for approx. 1.4 hrs | |
|---|---|---|---|---|
| Olanzapine Form I/Lot# | OVI in ppm Methanol | OVI in ppm Dichloromethane | OVI in ppm Methanol | OVI in ppm Dichloromethane |
| DR&D-1-33-20g | 59 | 1319 | 38 | 375 |
| DR&D-1-34-20g | 54170 | 15395 | 62 | 129 |
| DR&D-1-35-20g | 70561 | 15538 | 117 | 117 |
| DR&D-1-36-20g | 54657 | 2516 | 842 | 104 |
| DR&D-1-37-25g | 86666 | 3965 | 739 | 100 |

We claim:

1. Olanzapine pseudopolymorph Form E characterized by the listed "d" spacing:

| "d" spacing | Intensity (%) |
|---|---|
| 10.2393 | 100 |
| 5.4101 | 26 |
| 4.7016 | 31 |
| 4.4427 | 33 |
| 3.8490 | 33 | in powder X-ray diffractogram.

2. Olanzapine pseudopolymorph Form E characterized by the listed "d" spacing:

| |
|---|
| 10.2393 |
| 9.3935 |
| 7.0421 |
| 6.8319 |
| 6.2405 |
| 5.9907 |
| 5.7448 |
| 5.4101 |
| 5.2117 |
| 5.1037 |
| 5.0277 |
| 4.8060 |
| 4.7016 |
| 4.4427 |
| 4.3203 |
| 4.2594 |
| 4.0299 |
| 3.9605 |
| 3.8490 |
| 3.7855 |
| 3.7020 |
| 3.5956 |
| 3.5160 |
| 3.4282 |
| 3.2901 |
| 3.2339 |
| 3.1271 |
| 2.9886 |
| 2.9117 |
| 2.7893 |
| 2.7394 |
| 2.6566 |
| 2.6384 |
| 2.6051 |
| 2.5426 |
| 2.5034 |
| 2.4500 |
| 2.4136 |
| 2.3482 |
| 2.3033 |
| 2.2845 | in powder X-ray diffractogram.

3. A process for preparing a solvated polymorphic Form E of Olanzapine comprising:
   a) reacting 4-amino-2-methyl-10H-thieno[2,3-b][1,5]benzodiazepine HCl and 1-methylpiperazine in an aprotic high boiling solvent or mixtures thereof at a temperature of from between about 90° C. to about 130° C.;
   b) purifying the product of step a) in an acidic medium;
   c) basifying the product of step b) to a pH of from about 7.5 to about 8.5;
   d) extracting the product of step c) using a low boiling organic solvent;
   e) seeding with pure olanzapine Form I; and
   f) rapid crystallization with a mixture of methanol and dichloromethane while seeding.

4. The process of claim 3 wherein the step of rapid crystallization is completed in less than approximately two hour.

5. The process of claim 3 wherein the step of rapid crystallization is completed in less than approximately one hour.

6. The process of claim 3 wherein the step of rapid crystallization is completed in less than approximately 30 minutes.

7. The process of claim 3 wherein the reaction temperature is about 115° C. to about 120° C.

8. The process of claim 3 wherein the reaction temperature is about 110° C.

9. The process of claim 3 wherein the aprotic high boiling solvent is dimethyl sulfoxide.

10. The process of claim 3 wherein the low boiling organic solvent is selected from the group consisting of methanolic-dichloromethane mixture, diethylether, dichloroethane, chloroform, isopropanol-methylenechloride mixture, dichloromethane-methanol, dichloromethane, methanol-chloroform mixture, ethyl acetate or low polar ketonic solvents.

11. The process of claim 3 wherein the crystallization solvent is a mixture of methanol and dichloromethane in a ratio of methanol:dichloromethane of about 1:99 to about 10:90 parts by volume.

12. The process of claim 3 wherein the acidic medium is an organic acid.

13. The process of claim 12 wherein the organic acid is acetic acid or oxalic acid.

14. The process of claim 3 wherein the product of step c) is basified by adding sodium hydroxide.

15. The process of claim 3 further comprising crystallization of Olanzapine Form I by the steps of:
   g) adding a predetermined ratio of methanol-dichloromethane solvent;
   h) seeding the solution of step g) with Olanzapine Form I from about 0° to approximately 10° C.; and
   i) step-wise drying the product of step h) resulting in Olanzapine Form I.

16. The process of claim 15 further comprising a final drying at from about 40° C. to about 60° C. for approximately 1 to 3 hours.

17. The process of claim 15 wherein the step-wise drying comprises drying at room temperature and then drying in a rotary evaporator at about room temperature for approximately 6 to 8 hours and then at approximately 40° C. for approximately 1.4 to approximately 2 hours.

18. The process of claim 14 wherein the basification is carried out with approximately 40% aqueous sodium hydroxide at a temperature of from about 0° C. to about 10° C.

19. The process of claim 3 wherein the extracting solvent is a mixture of methanol and dichloromethane.

20. The process of claim 3 wherein the extracting solvent is dichloromethane.

21. The process of claim 3 wherein the extracting organic solvent is treated with basic activated charcoal.

22. The process of claim 21 where the extracting organic solvent is treated with basic activated charcoal for approximately 1 to 2 hours at temperature of from about 20° C. to about 40° C.

23. The process of claim 19 where the organic solvent is a mixture of methanol and dichloromethane having a methanol: dichloromethane ratio of from about 1:9 to about 3:7.

24. A method for preparing form I Olanzapine comprising mixing 4-amino-2-methyl-10H-thieno[2,3-b][1,5]benzodiazepine hydrochloride with a mixture of 1-methylpiperazine, dimethylsulfoxide; purifying the mixture with acetic acid; basifying the purified mixture with sodium hydroxide;

extracting the basified mixture with a solvent selected from the group consisting of from about 1.5 to about 15% (v/v) methanol-dichloromethane mixture and dichloromethane; reducing the extracted material to a predetermined critical volume; and rapidly crystallizing the reduced volume material by seeding with pure Olanzapine Form I in a mixture of methanol and dichloromethane within from about 20 minutes to about two hours at a temperature of from about 0° C. to about 10° C. to provide Olanzapine Form E followed by step-wise drying of the Olanzapine Form E to provide Olanzapine Form I.

25. A method of preparing Olanzapine Form I comprising subjecting the Olanzapine Form E of claim 2 to step-wise drying resulting in Olanzapine Form I.

26. The method of claim 25 wherein the step-wise drying further comprises drying in a rotary evaporator at room temperature for from about 6 to about 8 hours and then drying in a rotary evaporator at about 40° C. for from about 1 to about 2 hours.

27. Method for preparation of pure Olanzapine polymorphic Form I, characterized in that a solvated polymorphic Olanzapine Form E prepared by rapid crystallization in dichloromethane-methanol mixture at about 0° C. with continuous seeding with ultra pure Olanzapine polymorphic Form I is dried in a step-wise manner resulting in pure Olanzapine polymorphic Form I.

* * * * *